(12) United States Patent
Yue

(10) Patent No.: US 6,436,448 B1
(45) Date of Patent: Aug. 20, 2002

(54) METHOD FOR THE TREATMENT OF LYMPHEDEMA USING GUAIFENESIN

(75) Inventor: Samuel K. Yue, Edina, MN (US)

(73) Assignee: Sky BioHealth Solutions, Inc., Eden Prairie, MN (US)

( * ) Notice: Subject to any disclaimer, the term of this patent is extended or adjusted under 35 U.S.C. 154(b) by 0 days.

(21) Appl. No.: 09/891,136

(22) Filed: Jun. 25, 2001

(51) Int. Cl.$^7$ .................. A61K 35/78; A61K 31/075
(52) U.S. Cl. ............................ 424/725; 514/718
(58) Field of Search .................. 424/725; 514/718

(56) References Cited

U.S. PATENT DOCUMENTS

| | | | |
|---|---|---|---|
| 4,822,610 A | 4/1989 | Bush | 424/145 |
| 5,215,750 A | 6/1993 | Keane | 424/440 |
| 5,612,051 A | 3/1997 | Yue | 424/423 |
| 5,707,642 A | 1/1998 | Yue | 424/423 |
| 5,863,552 A | 1/1999 | Yue | 424/423 |
| 5,895,787 A | 4/1999 | Arffmann et al. | 514/415 |
| 5,916,183 A * | 6/1999 | Reid | 601/134 |
| 6,040,157 A * | 3/2000 | Hu et al. | 435/69.4 |
| 6,048,544 A | 4/2000 | Yue | 424/443 |
| 6,251,863 B1 | 6/2001 | Yue | 514/12 |

OTHER PUBLICATIONS

Website http://public.csusm.edu/public/guests/nancym/QandA.htm, "Questions & Answers for Guaifenesin User's", (Date Unknown).
Website http://public.csusm.edu/public/guests/nancym/FindingDosage.html, "Finding the Right Dosage", by Nancy Medeiros, Guaifenesin Advocate, 11/97.
Website http://public.csusm.edu/public/guests/nancym/Urico96.htm, "Use of Uricosuric Agents in Fribromyalgia (For Physicians)", by R. Paul St. Armand, M.D., 9/96.
Website http://public.csusm.edu/public/guests/nancym/AboutGuai1999.htm, "Fibromyalgia (For Patients)", by R. Paul St. Armand and Claudia Craig Marek, 1/99.
Website http://www.netromall.com/guai–support/basic_treatment.htm, International Guai–Support Group, "Basic Treatment Instructions", by Tesa Marcon, Rev. Dec. 8, 1999.
Website http://www.netromall.com/guai–support/uricorsuric_agents_fms.htm, International Guai–Support Group, "The Use of Uricosuric Agents in Fibromyalgia", by R. Paul St. Armand, (date unknown).
Website http://www.netromall.com/guai–support/hypoglycemia_diet.htm, International Guai–Support Group, "Dr. St. Armand's Diet for Hypoglycemia & Weight Reduction", by R. Paul St. Armand, Rev. Jun. 30, 2000.
Website http://www.netromall.com/guai–support/guai_sources.htm, "Guaifenesin Sources", International Guai–Support Group, Rev. Aug. 24, 2000.
Website http://www.netromall.com/guai–support/faq_guai–med.htm, International Guai–Support Group, "Guaifenesin Medication", (date unknown).
Website http://www.netromall.com/guai–support/how_guai_works.htm, International Guai–Support Group, "How Guai Works on FMS", Dr. R. Paul St. Armand (date unknown).
Website http://www.netromall.com/guai–support/success.htm, International Guai–Support Group, "Guaifenesin Success Stories", Rev. Jun. 12, 2000.
Website http://www.netromall.com/guai–support/1disease2names.htm, International Guai–Support Group, "One–Disease, Two Names", by R. Paul St. Armand (date unknown).
Website http://www.members.aol.com/SynergyHN/12c.html, "A Case History of FMS/CFIDS/MCS and the Roles of Guaifenesin, a Low Carbohydrade Diet and Enviromental Medicine in Recovery", by J.C. Warehouse (date unknown).

* cited by examiner

*Primary Examiner*—Raymond Henley, III
(74) *Attorney, Agent, or Firm*—Fredrikson & Byron, P.A.

(57) ABSTRACT

A novel method for preventing and treating lymphedema and for inducing weight-loss in a patient having an elevated protein concentration in the patient's by administering a therapeutically effective amount of guaifenesin or its analog to the patient. In one embodiment, the method further includes administering in the patient's diet an enzyme supplement chosen to increase the ability of the patient's gastrointestinal tract to digest food and administering to the patient an effective amount of relaxin hormone.

17 Claims, No Drawings

METHOD FOR THE TREATMENT OF LYMPHEDEMA USING GUAIFENESIN

FIELD OF THE INVENTION

The present invention relates to a novel method for the treatment of lymphedema and in reducing weight gain associated with lymphedema.

BACKGROUND OF THE INVENTION

The lymphatic system is a complex structure organized like the blood system in that it includes a system of numerous tiny vessels connected to a network of larger vessels, and through which system and network a liquid medium containing solutes and particulates is transferred. A healthy lymphatic system continuously drains lymphatic fluid, consisting of a mixture of lymph, water, proteins and other matter, away from various interstitial areas of the body and back into the blood system. Lymph is the clear, liquid medium or solvent of the lymphatic system.

In contrast to the blood system, which utilizes the heart to pump blood throughout the body, the lymph fluid is pumped through the lymphatic system and away from various body areas by both the action of adjacent muscle tissue and the contraction of the larger lymphatic vessels. Foreign matter is filtered out of the lymph fluid as the fluid passes through bundles of lymph nodes during its course through the lymphatic system. The lymph nodes also monitor the contents of the lymph fluid to determine if any appropriate immune reactions should be initiated by the host's immune system. The lymphatic vessels are not interconnected in the same manner as blood vessels, but rather form a set of coordinated structures including the initial lymphatic sinuses which drain into the lymphatic capillaries and subsequently to the collecting lymphatics which drain into the lymphatic trunks and the thoracic duct which ultimately drains into the blood system after the filtration.

Lymphedema or "high protein edema" is a deficiency, blocking or dysfimction of the lymphatic system that limits the flow of lymph fluid from a body area. Any sustained accumulation of proteins delivered to the body tissue by the blood capillaries, and not removed by the lymphatic system, will cause an accumulation of high protein fluid in the interstitial areas of the body tissues resulting in lymphedema or "high protein edema".

Fibromyalgia patients and some normal people develop lymphedema commonly labeled as "subjective swelling" of unknown etiology. Though often dismissed as subjective, many of these patients have overt swelling on their body that is not amenable to conventional medical treatment—i.e. diuresis through diuretics. These swellings often complicate many of the fibromyalgia patients' daily living which includes swelling of the upper and lower extremities, faces and jaws and trunks. In the more severe cases, the lymphedema may result in swelling of the lung tissues causing shortness of breath and complicating the oxygen transfer process within the lung linings. It may also cause swelling of the heart lining causing pericardial effusion and impede the pumping mechanism of the heart.

In addition to these troublesome swellings, excessive fluid retention within the tissues also impacts the ability of many of these patients to recover from skin and superficial injuries and infections. The fluid retention also increases the risks associated with surgery because effusion of fluid into an incision site complicates the recovery process. As these patients age and the disease progresses, the normal healing process of their bodies (particularly the extremities) is impeded by the swelling, which results in pooling of the fluid to the extremities. This swelling and pooling of fluid on the extremities puts compressive pressure on the blood vessels and impedes the blood flow in the extremities, which further reduces the circulation and slows the healing process.

Conventional treatment techniques for lymphedema include the use of manual lymph drainage techniques, compression techniques, electrical stimulation of the lymph vessels and exercise.

SUMMARY OF THE INVENTION

The present invention is based upon the recognition that a relationship exists between the porosity (altered permeability or changed selectivity) of a person's gastrointestinal tract ("GI tract") and its diseased ability to absorb partially-digested food (macronutrients, in the form of partially digested proteins or large clumps of amino acid) to the accumulation of high protein fluid in a patient's tissues resulting in weight gain and lymphedema.

Accordingly the ideal treatment for this type of lymphedema comprises: (1) restoring the selectivity or altered permeability of the mucosa within the linings of the GI tract, thus, reducing its ability to absorb partially digested proteins; and (2) treating the previously accumulated high protein edema or lymphedema.

In accordance with one aspect of the invention it has been surprisingly found that guaifenesin is useful in reducing the accumulation of fluid in a patient's tissue and in the treatment of lymphedema.

In one method of the invention, the accumulation of fluids in the tissue of a patient having such accumulation is reduced by administering to the patient a therapeutically effective amount of guaifenesin or one of its pharmaceutically acceptable derivatives. In one embodiment of the method, the amount administered is about 600 mg to about 4000 mg per day.

In one preferred embodiment of the invention, the guaifenesin or its pharmaceutically acceptable derivative is administered to the patient in two different dosage forms, one dosage form being a short acting form and the other being a long acting form. The short acting dosage is preferably about 200–600 mgs and the long acting form is preferably about 200–600 mgs. The two forms are desirably administered to the patient once or twice a day so that a sustained level of guaifenesin or its pharmaceutically acceptable derivative may be obtained in the blood stream sufficient for the lymphatic diuresis to occur.

In other embodiments of the invention, the guaifenesin or its pharmaceutically acceptable derivative may be administered to the patient in more than one dose of a short acting dosage form or in different combinations of short acting doses with long acting doses. Some reduction of fluid accumulation will be seen with the administration of guaifenesin in the amounts described herein in most patients, however, the dosage regime should be optimized for each patient.

Another embodiment of the invention is a method for inducing weight loss in patients having accumulated fluid in their tissue comprising administering an effective amount of guaifenesin or one of its pharmaceutically acceptable derivatives to a patient to cause a reduction in the amount of the accumulated fluid and weight loss.

Yet another embodiment of the invention is a method for treating and preventing lymphedema comprising the steps of: a) using guaifenesin or one of its pharmaceutically acceptable derivatives to reduce accumulated high protein fluid in a patient; b) including in the patient's diet, enzyme supplements chosen to increase the ability of the patient's gastrointestinal tract to digest food; and c) administering to the patient an effective amount of relaxin and its related hormones to induce production of new collagen to repair the mucosa and restore the selectivity of the gastrointestinal tract.

DETAILED DESCRIPTION OF PREFERRED EMBODIMENTS

Lymph edema is an interesting component of fibromyalgia. Lymphedema is also very common in the general population. Based on clinical observation of fibromyalgia patients and general population, the inventor believes that much of the subjective swelling in many women during the premenstrual cycle is related to this particular problem of swelling of the lower extremities and the abdomen region. As many as 5–10 lbs of fluid may be accumulated within these tissues in the normal population of women who experience premenstrual subjective swelling. Classic lymphedema described in most medical text is related to the mechanical blockage of the lymphatic drainage, particularly of the extremities. A classic example is filariasis or elephantiasis, a form of parasitic infestation that affects and destroys mostly the lymphatic vessels. This results in blockage of lymphatic drainage and swelling of the lower extremities where the blockage occurs. No satisfactory treatments are available for this difficult problem of local mechanical blockage of the lymphatic drainage system. Furthermore, any cut or scratch on the skin will cause a significant oozing of lymphatic fluid which may lead to severe infections and its complications.

Another classic example of lymphedema is the result of radical mastectomy surgery. Radical mastectomy, where the pectoralis major and minor muscles, lymph nodes are removed together with the breast, induces mechanical blockage of the lymphatic drainage within these patients' axillary area. The resulting obstruction of lymphatic drainage of the upper arm causes uncomfortable swelling on that side of the arm. No effective medical treatments are available. Manual manipulation and compression may be used to help facilitate drainage to reduce the degree of the swelling.

The inventor believes that lymphedema or swelling due to high protein fluid accumulation within the tissues of the body can be found in much of the general population. However, fibromyalgia patients in particular experience this problem to a much greater extent and intensity. Many fibromyalgia experts do not believe that these patients have any physiological reason for the swelling and therefore dismiss the edema complaint as subjective swelling. The inventor has observed true swelling of various degree in these patients and also observed this type of swelling in the general diseased and well population. The inventor believes that the swelling is caused by the accumulation of fluids in tissue as a result of a high protein concentration within the interstitial tissue that causes fluid to be drawn into the tissue.

The inventor believes that the fluid accumulation in the tissues and resultant swelling in fibromyalgia patients and others in the general population is related to the altered permeability of the mucosa within the GI tract, i.e. changes of the selectivity of the mucosa within the lining of the GI tract.

Because of changed selectivity and altered permeability, the GI tract is rather porous in many fibromyalgia patients and some of the general population. The term "leaky gut" has been used to describe this condition. Many practitioners hypothesize that the daily grinding of food particles within the GI tract easily injures the mucosa on these susceptible patients. Once the mucosa is injured, many of the undigested or partially digested proteins in the form of macronutrients are allowed to leak through the porous mucosa into the systemic circulation. One other area of altered permeability or changed selectivity that occurs in these patients is located within the capillary membranes. Macronutrients diffuse or "leak" from the capillary membranes into the interstitial space within the tissues to be later drained into the lymphatic system. These undigested macronutrients move slowly through the tissues, are toxic to the body and treated by the body's immune system as foreign antigen. Antigen-antibody reactions occur within the lymphatic system and the antigen-antibody complexes are trapped within the lymph nodes further delaying lymphatic drainage and aggravating the swelling. This is the most likely explanation for the numerous complaints of the fibromyalgia patients that the lymph nodes are often swollen and painful and that they seem to have an immune response indicative of frequent infections but with no overt or frank infections within the body.

The inventor has also observed that fibromyalgia patients often have skin lesions that continuously break down and heal and then the cycle repeats itself in another area. The cause of such break down of skin lesions is not known. The inventor believes that the skin on the fibromyalgia patient is similar to the mucosa, with skin deriving from ectoderm and the mucosa deriving from the endoderm. It appears that the skin lesions and mucosa lesions do occur on these patients secondary to many etiologies. One of them could be from the daily grinding of the food particles within the GI tract. The skin on the fibromyalgia patient and the mucosa on the lining of the GI tract of the fibromyalgia patient are both made up of collagen, the production of which is regulated in whole or in part by the relaxin hormone. It is the inventor's belief that in patients with deficiency of the relaxin hormone the quality of collagen produced is poor resulting in the skin or the mucosa being easily irritated and more prone to injury and therefore susceptible to wear and tear of daily living. Skin and mucosa with poor quality collagen also heal slowly.

The inventor believes that the mucosa of the GI tract behaves similarly when there is a deficiency of relaxin hormone. Collagen is a major component of the mucosa. Poor quality collagens within the mucosa accelerate the daily wear and tear of the digestive processes. The end result is lesions, pores or gaps between the cells within the mucosa of sufficient size to allow macronutrients to leak through. It has been shown that in fibromyalgia patient the mucosa reacts somewhat differently than normal people in the form of dysautonomia or excessive opening of the mucosa sieve that serves as normal filtering function. The inventor believes that when the integrity of the mucosa is compromised, as in fibromyalgia patients or in some patients in the general population without fibromyalgia, the mucosa will not be able to prevent certain types of food or partially broken down proteins or clumps of amino acids from escaping through the mucosa into the systemic circulation. One example of this is the protein casein, which is known to be circulating in the blood stream of rheumatoid arthritis patients. Casein should be found circulating only in a lactating mothers' blood stream. The inventor believes that casein is found in the blood stream of these other patients because of the incomplete digestion of dairy products combined with an abnormally porous mucosa allowing the casein to penetrate the mucosa and circulate in the blood stream. Once the casein protein enters the blood stream and is later "leaked" into the tissues and the lymphatic vessels from the capillary membranes, an antigenantibody reaction ensues with its associated immune responses. The immune responses are often classified as delayed hypersensitivity reactions but the swelling within the tissues and the lymphatic nodes and vessels which accompany such a reaction is usually ignored. Similar observations of symptoms in certain individuals have been made, from time to time, which are associated with the ingestion by the individual of certain types of food, e.g., gluten in wheat and casein in dairy products.

Once the macronutrients and proteins "leak out" of the GI tract, the inventor believes that only a portion of them are detoxified or broken down in the liver through enzyme degradation into amino acids that may be utilized by the body. The inventor believes that a large portion of these clumps of protein is circulated to the end capillary membranes and "leaked" to the tissues. These trapped proteins move slowly in the patient's tissue and are unable to pass through the tissue with ease. Accumulation of these clumps of amino acid in the form of small protein particles within the tissues exerts osmotic pressure to draw fluid into the tissues causing swelling. It is commonly labeled as high protein edema, a type of edema within the lymphatic drainage system, therefore, not amenable to diuretic treatment because of its non-cardiac origin.

Since this process is ongoing and dynamic, fibromyaglia patients and patients in the general population with such trapped macronutrients gain water weight and accumulate fluid in their entire body. Many physicians perceive this weight gain as resulting from excessive sugar or other caloric intake by these patients. However, many of these patients report that at times they have rapid weight gain disproportionate to the amount of food or calories they consume and at other times they lose a disproportionate amount of weight without dieting. The inventor believes that the lymphedema or swelling of many of these fibromyalgia patients and the individuals in the general population is a result of mucosa inadequacy or porosity of the mucosa and the GI tract's inability to prevent clumps of amino acids or macronutrients from penetrating the mucosa. This process is often exaggerated by a type of offending food consumed by the patient. Some individuals have difficulty digesting certain food types, such as wheat or dairy products. Overindulging in one particular type of such food may cause excessive swelling and avoiding the consumption of that food will reduce the swelling. The inventor has observed that some of these patients will continue to gain weight even when placed on restricted 1,000 calorie or starving diet within a rigid and control environment in a hospital if they consume certain food types.

One embodiment of this invention is directed to a method for treating and preventing lymphedema in patients comprising: a) administering supplemental enzymes to the patient at mealtimes, the supplemental enzymes being chosen for their ability to aid the patient's GI tract to properly and fully digest food, and therefore, reduce or eliminate the presence of clumps of amino acids or macronutrients which if they penetrate the mucosa may be trapped and result in fluid accumulation in the tissues; b) administering to the patient a therapeutically effective amount of guaifenesin or one of its pharmaceutically acceptable derivatives to reduce fluid accumulation in the patient; and c) administering to the patient an effective amount of relaxin hormone to induce production of new collagen in the mucosa of the GI tract to repair the altered permeability and the changed selectivity.

A first step in a method of this invention is designed to help these patients digest food to the fullest extent, i.e. protein intake needs to be digested completely to amino acid. Supplemental enzymes will be administered to the patient at mealtimes, and at other appropriate time to help these patients digest their food. Supplemental enzymes useful with this invention are chosen to specifically address the digestive activity of these patients Therefore, the supplemental enzymes are desirably taken together with food. Enzymes and enzyme supplements useful with this invention includes some fruit enzymes, for example, bromelain, papain, rutin, among others and animal enzymes, pancreatin, trypsin, chymotrypsin and others. Commercially available enzymes of single fruit/vegetable/animal or in various ratios of combined fruit/vegetable/animal are available. Enzyme supplements, manufactured by various manufacturers, include for example, Wobenzym® (a registered trademark of Mucos Emulsions GMBH) N enzyme supplements manufactured by Mucos Emulsions GMBH &Co of Germany, Creon® (a registered trademark of Kali-Chemie Pharma GMBH) enzymes manufactured by Kali-Chemie Pharma GMBH, Germany, and Viokase® (a registered trademark of A.H. Robins Company, Incorporated) and Pancrease® (a registered trademark of Johnson & Johnson) enzymes both manufactured by Ortho-McNeil Pharmaceutical. Many over-the-counter enzymes can be used to help these patients digest their food to their fullest extent. It is particularly important to digest all protein to its fullest extent, so that animal enzymes such as lipase, trypsin, chymotrypsin and pancreatin enzymes, which digest protein, are more useful in the method of this invention than other enzymes.

One additional added benefit of using digestive enzyme is the effect of better digestion on the GI tract, on the colon pH and sugar content. By digesting the food properly and to its fullest extent, the changed pH and elevated sugar level within the environment of the colon is restored back to normal. Once restored, normal bacterial flora will be encouraged to return and the candida or yeast infection or overgrowth often seen in these patients minimized. The inventor has observed in many cases that once these patients have been on supplemental enzymes for a brief period of time their fungal infection or overgrowth is no longer a problem for them. This is a natural way of treating the fungal infection or overgrowth by promoting the proliferation of healthy bacteria and restoring the normal bowel flora.

Once the GI tract is normalized, another step of a method of the invention is to treat the lymphedema and to reduce fluid accumulation in the tissue. In a preferred method of the invention it has been found that fluid accumulation in tissue and the resulting lymphedema may be treated by administering to the patient an effective amount of guaifenesin or a pharmaceutically acceptable derivative thereof sufficient to reduce fluid accumulation.

Guaifenesin has been used to treat fibromyalgia. One advocate of its use has been Dr. Paul St. Amand. Dr. St. Amand believes that guaifenesin works by interfering and eliminating the accumulated calcium phosphate within the cell in the tissues. The following quote was found on a guaifenesin user support website found at www.guaifenesin.com:

"Dr St Amand's working hypothesis is that people with fibromyalgia have an inherited abnormality in phosphate excretion. People with fibromyalgia are born with the gene(s) for fibromyalgia and over time the phosphates accumulate in the mitochondria of cells throughout the body. Eventually enough phosphates are accumulated to produce the symptoms of fibromyalgia.

In simple terms, guaifenesin works in people who have fibromyalgia by withdrawing the phosphates from the cells of the muscles, tendons, joints, brain, intestinal tissues, endocrine glands and many other sites and allowing the phosphates to be excreted via the kidneys."

The inventor disagrees with the basic assumption and hypothesis on the inner working of guaifenesin. The inventor believes that guaifenesin's activity is its ability to break down undigested protein, and antigen-antibody complexed protein within the tissues and lymphatic nodes and vessels to reduce fluid accumulation and therefore reduce lymphedema. Guaifenesin is an expectorate and it thins out proteinaceous secretions from our lungs by directly and/or indirectly through stimulating macrophages to breaking the proteins into its amino acids components. The inventor believes that guaifenesin break down the proteins within the blood stream, tissues, and the lymphatic system. By maintaining a high level of guaifenesin within the blood stream, the "foreign" proteins within the tissue, antigen-antibody protein complexes within the lymph nodes will be broken down allowing the broken down amino acid particles to diffuse across the tissue into the lymphatic drainage. With this fluid switch from the lymphatic to the systemic circulation diuresis ensues without affecting the potassium metabolism within the kidney. The inventor has also observed lymphedema that occurs in non-fibromyalgia patients that responds well to guaifenesin therapy resulting in reduction of the swelling. Fibromyalgia patients on guaifenesin have also been observed to have reduction of the painful and swollen lymph nodes. They have also been observed to have different rate of swelling reduction of one extremity versus the other, with the more swollen extremity slowly catching up with the other over time. These observations confirm the hypothesis that guaifenesin works on the "foreign" protein or antigen-antibodies protein complexes within the tissues and lymphatic system. With different size "foreign" protein and antigen-antibody protein complexes, guaifenesin's action on these proteins in various part of the body will proceed with different rate resulting in different rate of swelling reduction in different part of the bodies.

Many of these patients, however, are diagnosed by a physician to have a cardiogenic etiology of edema and are typically treated with diuretics of various types. Cardiogenic edema should respond to a diuretic within two to three months. The inventor has observed patients being on diuretics for as long as a year with no results on the lymphedema.

In testing this hypothesis, the inventor has used guaifenesin on over several hundred patients in varying dosages. The inventor has found that dosages of about 600 mg to about 4000 mg per day may result in reduction of accumulated fluid.

Guaifenesin is also available in sustained-release version. The long-acting version is typically available at 600 mg and is designed to be taken two or three times a day. The long-acting version of guaifenesin may not work well in some patients due to absorption problems. The inventor has found that combination of short acting and long acting versions improves the results. Other combinations of various dosage for ms may be used with various patients to improve results. Preferably, a combination of an effective short-acting form with an equally effective long-acting form of guaifenesin will be administered three times a day.

While the inventor has only administered guaifenesin to patients orally, guaifenesin and its analogs can be formulated using known methods to prepare pharmaceutically useful compositions by combining guaifenesin with a pharmaceutically acceptable carriers and adapted to be administered by injection, transdermally, transmucosally or by any other means of drug delivery vehicle. Guafenesin may also be administered to a patient in a patch form or in a cream, ointment, or in a nasal or lung spray, or in a suppository.

A therapeutically effective amount defines an amount resulting in the improvement of a physiologic condition to be treated. The actual dose will differ with the patients overall condition, the seriousness of the symptoms, contraindications, etc. The determination of the effective dose is well within the skill of a practicing physician or pharmaceutical practitioner. The dose will also vary depending the route of administration, formulation method, patient age and medical history, and the overall administration schedule to be employed.

Herbal medicines, both western and Chinese, have been used to treat lymphedema with some success. Many herbal medications contain coumarin or similarly related molecules. These molecules have been shown to decrease some of the swelling associated with lymphedema indirectly through the stimulation of macrophages. Other herbal medications also have been used successfully in reducing the swelling of lymphedema but the mechanism of action remains unclear. One example of such an herbal remedy is horse chestnut extract, which seems to be able to reduce the lymphedema in some patients by scavenging the foreign proteins within the body and breaking it down to amino acids. . Two other western herbs, golden ash and goldenrod, also are able to reduce some swelling, indirectly, through stimulation of macrophage activity and scavenging and breaking down the protein within the tissue. A whole list of Chinese herbal medications are listed below which are categorized in Traditional Chinese Medicine for their ability to reduce "wind and dampness" (swelling) and/or perform diuresis in the body.

Wind-Dampness Eliminating Medicines

Bungarus Parvus

Caulis Erycibes

Caulis Piperis Futokadsurae

Caulis Sinomenii

Caulis Spatholobi

Caulis Trachelospermi

Cortex Acanthopanacis Radicis .

Cortex Erythrinae

Faeces Bombycis

Folium Clerodendri Trichotomi

Fructus Chaenornelis

Herba Siegesbeckiae

Os Tigris

Radix Aconiti

Radix Angelicae Pubescentis

Radix Aristolochiae Fangchi

Radix Clematidis

Radix Cynanchi Paniculati

Radix Dipsaci

Radix Gentianae Macrophyllae

Radix Stephaniae Tetrandrae

Radix Tripterygii Wilfordii

Ramulus Mori

Ramulus Taxilli

Ramulus Wallichii seu Puberulii

Rhizoma Cibotii
Rhizoma Dioscoreae Nipponicae
Rhizoma Drynariae
Rhizoma Smilacis Chinensis
Zaocys
Diuretics
  Caulis Akebiae
  Exocarpium Benincasae
  Folium Pyrrosiae
  Fructus Kochiae
  Herba Artemisiae Scopariae
  Herba Desmodii Styracifolii
  Herba Desmodii Triquertri
  Herba Dianthi
  Herba Gnaphalii Affinis
  Herba Hyperici Japonici
  Herba Lobeliae Chinensis
  Herba Lysimachiae
  Herba Polygoni Avicularis
  Herba Sambuci Chinesis
  Herba Sedi Sarnentosi
  Polyporus Umbellatus
  Poria
  Rhizoma Alismatis
  Rhizoma Dioscoreae Hypoglaucae
  Rhizoma Polygoni Cuspidati
  Semen Abutili
  Semen Coicis
  Semen Phaseoli
  Semen Plantaginis
  Spora Lygodii
  Stigma Maydis In one method of invention, guaifenesin may be combined at various dosages with one or more of the above herbs to potentiate the swelling reducing effects of both herbs and guaifenesin on the lymphedema.

How guaifenesin works on the swelling is at present unclear. It may directly break down the protein or indirectly stimulate the macrophage to engulf the protein and then break the protein down. Regardless of the route of activities, once the action of the guaifenesin on the protein is ascertained, guaifenesin-like molecules can be manufactured with improved activity so that more efficient and effective molecules may be available. Therefore any analog with enhanced guaifenesin-like activities can be invented or manufactured to break down these proteins within the tissue to decrease the lymphedema on these unfortunate patients with ease.

In one method of the invention, the method for treating and preventing lymphedema further includes administering to a patient a therapeutically effective amount of relaxin hormone to increase the ability of the GI tract to produce new collagen that will decrease the porosity of the mucosa. The use of relaxin hormone to increase rebuild collagen is described in U.S. Pat. No. 6,048,544, which is hereby incorporated in its entirety. The inventor believes that the lack or insufficient amount of relaxin in these patients causes increased porosity of the GI tract. Thus, replacing the relaxin will then afford good collagen within the mucosa, allowing the mucosa to act and function normally in addition to exerting its effect on other parts of the body. So once this is taken care of, the digestive problem and the lymphedema should subside with the treatment of the enzyme, the anti-lymphatic agents, and also the relaxin replacement to restore the porosity or malabsorption problem of the GI tract mucosa.

What is claimed is:

1. A method for treating lymphedema in a patient comprising administering a therapeutically effective amount of guaifenesin to the patient in two different dosage forms.

2. The method of claim 1 wherein the amount administered is about 600 mgs to about 4000 mgs per day.

3. The method of claim 1 wherein one dosage form is a short acting form and another dosage form is a long acting form.

4. The method of claim 3 wherein the amount administered in the short acting form is between 200 to 600 mgs and the amount administered in the long acting form is between 200 to 600 mgs.

5. The method of claim 4 wherein the amount administered in the short acting form is 200 mgs and the amount administered in the long acting form is 600 mgs.

6. The method of claim 1 wherein the step of administration comprises oral administration.

7. The method of claim 1 wherein the step of administration comprises administration by injection.

8. The method of claim 1 wherein the step of administration comprises transdermal administration.

9. The method of claim 8 wherein the step of administration comprises administration transdermally through a skin patch, cream or ointment.

10. The method of claim 1 wherein the step of administration comprises transmucosal administration.

11. The method of claim 10 wherein the step of administration comprises administration transmucosally through a nasal or lung spray or a suppository.

12. A method for inducing weight loss in a patient having accumulated fluid in tissue comprising administering to the patient an amount of guaifenesin sufficient to induce weight loss and reduction in the amount of accumulated fluid in at least two different dosage forms.

13. A method for treating and preventing lymphedema in a patient associated with an elevated protein concentration in the patient's tissue comprising:
  a. including in the patient's diet an enzyme supplement chosen to increase the ability of the patient's gastrointestinal tract to digest food;
  b. administering to the patient a therapeutically effective amount of a composition chosen to reduce fluid accumulation in the patient's tissue; and
  c. administering to the patient an effective amount of relaxin hormone to induce production of new collagen in the gastrointestinal tract.

14. The method of claim 13 wherein the composition chosen to reduce fluid accumulation in the patient's tissue is guaifenesin.

15. A method for treating lymphedema in a patient comprising of administrating effective amount of guaifenesin together with an herbal medication chosen because of its ability to reduce fluid accumulation in a patient's body wherein the amount of the herbal medication is sufficient to increase the overall swelling reduction effect.

16. A composition for use in reducing fluid accumulation in a patient's body comprising a therapeutically effective amount of guaifenesin combined with an herbal medication chosen for its ability to reduce fluid accumulation, wherein the amount of the herbal medication is sufficient to increase the overall swelling reduction effect.

17. The composition of claim 16 wherein the herbal medication is one of the herbal medications from the group consisting of: Bungarus Parvus, Caulis Erycibes, Caulis Piperis Futokadsurae, Caulis Sinomenii, Caulis Spatholobi, Caulis Trachelospermi, Cortex Acanthopanacis Radicis, Cortex Erythrinae, Faeces Bombycis, Folium Clerodendri Trichotomi, Fructus Chaenomelis, Herba Siegesbeckiae, Os Tigris, Radix Aconiti, Radix Angelicae Pubescentis, Radix Aristolochiae Fangchi, Radix Clematidis, Radix Cynanchi Paniculati, Radix Dipsaci, Radix Gentianae Macrophyllae, Radix Stephaniae Tetrandrae, Radix Tripterygii Wilfordii, Ramulus Mori, Ramulus Taxilli, Ramulus Wallichii seu Puberulii, Rhizoma Cibotii, Rhizoma Dioscoreae Nipponicae, Rhizoma Drynariae, Rhizoma Smilacis Chinensis, Zaocys, Caulis Akebiae, Exocarpium Benincasae, Folium Pyrrosiae, Fructus Kochiae, Herba Artemisiae Scopariae, Herba Desmodii Styracifolii, Herba Desmodii Triquertri, Herba Dianthi, Herba Gnaphalii Affinis, Herba Hyperici Japonici, Herba Lobeliae Chinensis, Herba Lysimachiae, Herba Polygoni Avicularis, Herba Sambuci Chinesis, Herba Sedi Sarmentosi, Polyporus Umbellatus, Poria, Rhizoma Alismatis, Rhizoma Dioscoreae Hypoglaucae, Rhizoma Polygoni Cuspidati, Semen Abutili, Semen Coicis, Semen Phaseoli, Semen Plantaginis, Spora Lygodii, and Stigma Maydis.

\* \* \* \* \*